US012566139B2

(12) United States Patent
Kakegawa et al.

(10) Patent No.: US 12,566,139 B2
(45) Date of Patent: Mar. 3, 2026

(54) METHOD ANALYSIS EMPLOYING MEASUREMENT BASED ON POLARIZATION ANISOTROPY

(71) Applicants: CANON KABUSHIKI KAISHA, Tokyo (JP); CANON MEDICAL SYSTEMS CORPORATION, Tochigi (JP)

(72) Inventors: Norishige Kakegawa, Tokyo (JP); Takahiro Masumura, Tochigi (JP); Fumio Yamauchi, Kanagawa (JP); Kengo Kanazaki, Kanagawa (JP); Tomohiro Nakamura, Saitama (JP); Ikuo Nakajima, Tokyo (JP); Teigo Sakakibara, Tokyo (JP)

(73) Assignees: Canon Kabushiki Kaisha, Tokyo (JP); Canon Medical Systems Corporation, Tochigi (JP)

( * ) Notice: Subject to any disclaimer, the term of this patent is extended or adjusted under 35 U.S.C. 154(b) by 458 days.

(21) Appl. No.: 18/310,615

(22) Filed: May 2, 2023

(65) Prior Publication Data
US 2023/0366826 A1     Nov. 16, 2023

(30) Foreign Application Priority Data

May 13, 2022    (JP) ................................. 2022-079531
Apr. 25, 2023    (JP) ................................. 2023-071430

(51) Int. Cl.
*B01L 3/00*        (2006.01)
*B01D 15/08*       (2006.01)
(Continued)

(52) U.S. Cl.
CPC ......... *G01N 21/76* (2013.01); *G01N 21/6428* (2013.01); *G01N 33/0073* (2013.01)

(58) Field of Classification Search
CPC .............. G01N 21/76; G01N 21/6428; G01N 33/0073; G01N 33/5306; G01N 33/542; G01N 2021/7786; G01N 21/6445
See application file for complete search history.

(56) References Cited

U.S. PATENT DOCUMENTS 4,492,762 A * 1/1985 Wang ................... G01N 33/582
                                                         436/536
4,516,856 A    5/1985 Popelka
(Continued)

FOREIGN PATENT DOCUMENTS

JP          3-52575 B2     8/1991
JP          3-188374 A     8/1991
(Continued)

OTHER PUBLICATIONS

Communication Pursuant to Article 94(3) EPC in European Application No. 23 172 752.0 (Oct. 2025).
(Continued)

*Primary Examiner* — Jennifer Wecker
*Assistant Examiner* — Oyeleye Alexander Alabi
(74) *Attorney, Agent, or Firm* — Venable LLP

(57) ABSTRACT

To perform measurement based on polarization anisotropy in which a reaction between a target substance and a luminescent reagent is performed within a short period of time, and in which high-sensitivity measurement can be performed, provided is an analysis method including measuring a value (R) for polarization anisotropy through use of a luminescent reagent that reacts with a target substance, to thereby determine at least any one of the presence or absence of the target substance and a concentration of the target substance, the analysis method including: a reaction step of mixing a sample containing the target substance with the luminescent reagent, and subjecting the mixture to a reaction to obtain a reaction liquid; a dilution step of diluting the (Continued)

REACTION STEP OF MIXING SAMPLE CONTAINING TARGET SUBSTANCE WITH LUMINESCENT REAGENT, AND SUBJECTING MIXTURE TO REACTION TO OBTAIN REACTION LIQUID

DILUTION STEP OF DILUTING REACTION LIQUID TO OBTAIN DILUTED LIQUID

MEASUREMENT STEP OF MEASURING R OF DILUTED LIQUID reaction liquid to obtain a diluted liquid; and a measurement step of measuring the R of the diluted liquid, the luminescent reagent including luminescent particles.

9 Claims, 6 Drawing Sheets

(51) Int. Cl.

| | |
|---|---|
| *B01F 33/302* | (2022.01) |
| *B01F 33/3033* | (2022.01) |
| *B01J 20/285* | (2006.01) |
| *B01J 20/287* | (2006.01) |
| *B01J 20/32* | (2006.01) |
| *B01L 7/00* | (2006.01) |
| *B01L 9/00* | (2006.01) |
| *B65G 47/80* | (2006.01) |
| *B82Y 20/00* | (2011.01) |
| *B82Y 30/00* | (2011.01) |
| *B82Y 40/00* | (2011.01) |
| *C12M 1/34* | (2006.01) |
| *C12M 3/06* | (2006.01) |
| *C12N 1/14* | (2006.01) |
| *C12N 1/20* | (2006.01) |
| *C12Q 1/02* | (2006.01) |
| *C12Q 1/6806* | (2018.01) |
| *C12Q 1/6844* | (2018.01) |
| *C12Q 1/6848* | (2018.01) |
| *C12Q 1/686* | (2018.01) |
| *G01N 15/10* | (2024.01) |
| *G01N 15/14* | (2024.01) |
| *G01N 15/1433* | (2024.01) |
| *G01N 21/29* | (2006.01) |
| *G01N 21/33* | (2006.01) |
| *G01N 21/64* | (2006.01) |
| *G01N 21/65* | (2006.01) |
| *G01N 21/76* | (2006.01) |
| *G01N 30/02* | (2006.01) |
| *G01N 30/60* | (2006.01) |
| *G01N 30/72* | (2006.01) |
| *G01N 33/00* | (2006.01) |
| *G01N 33/50* | (2006.01) |
| *G01N 33/543* | (2006.01) |
| *G01N 33/557* | (2006.01) |
| *G01N 33/574* | (2006.01) |
| *G01N 33/58* | (2006.01) |
| *G01N 33/68* | (2006.01) |
| *G01N 35/00* | (2006.01) |
| *H05B 45/10* | (2020.01) |

(56) References Cited

U.S. PATENT DOCUMENTS

| | | | |
|---|---|---|---|
| 6,159,750 A | 12/2000 | Edmonds | |
| 2009/0317922 A1* | 12/2009 | Levison | G01N 33/5306 |
| | | | 436/517 |
| 2021/0341488 A1 | 11/2021 | Fukuyama et al. | |

FOREIGN PATENT DOCUMENTS

| | | |
|---|---|---|
| JP | 2893772 B2 | 5/1999 |
| KR | 20180106684 A | 10/2018 |

OTHER PUBLICATIONS

Kathryn S. Schwenzer et al., "Automated Fluorescence Polarization Immunoassay for Monitoring Vancomycin," 5(3) Ther. Drug Monit. 341-345 (Sep. 1983) (XP000577456).

David M. Jameson et al., "Fluorescence Polarization/Anisotropy in Diagnostics and Imaging," 110(5) Chem. Rev. 2685-2708 (May 2010) (XP055243358).

Tatsuo Aikawa et al., "Polystyrene Latex Particles Containing Europium Complexes Prepared by Miniemulsion Polymerization Using Bovine Serum Albumin as a Surfactant for Biochemical Diagnosis," 145(3) Colloids Surf., B. 152-159 (May 2016) (XP029640038).

Jixi Zhang et al., "Semiconducting Polymer Encapsulated Mesoporous Silica Particles with Conjugated Europium Complexes: Toward Enhanced Luminescence under Aqueous Conditions," 6(21) ACS Appl. Mater. Interfaces 19064-19074 (Oct. 2014) (XP055644974).

Extended European Search Report in European Application No. 23172752.0 (Oct. 2023).

U.S. Appl. No. 18/310,005, filed May 1, 2023, Kakegawa et al.

* cited by examiner

FIG. 2

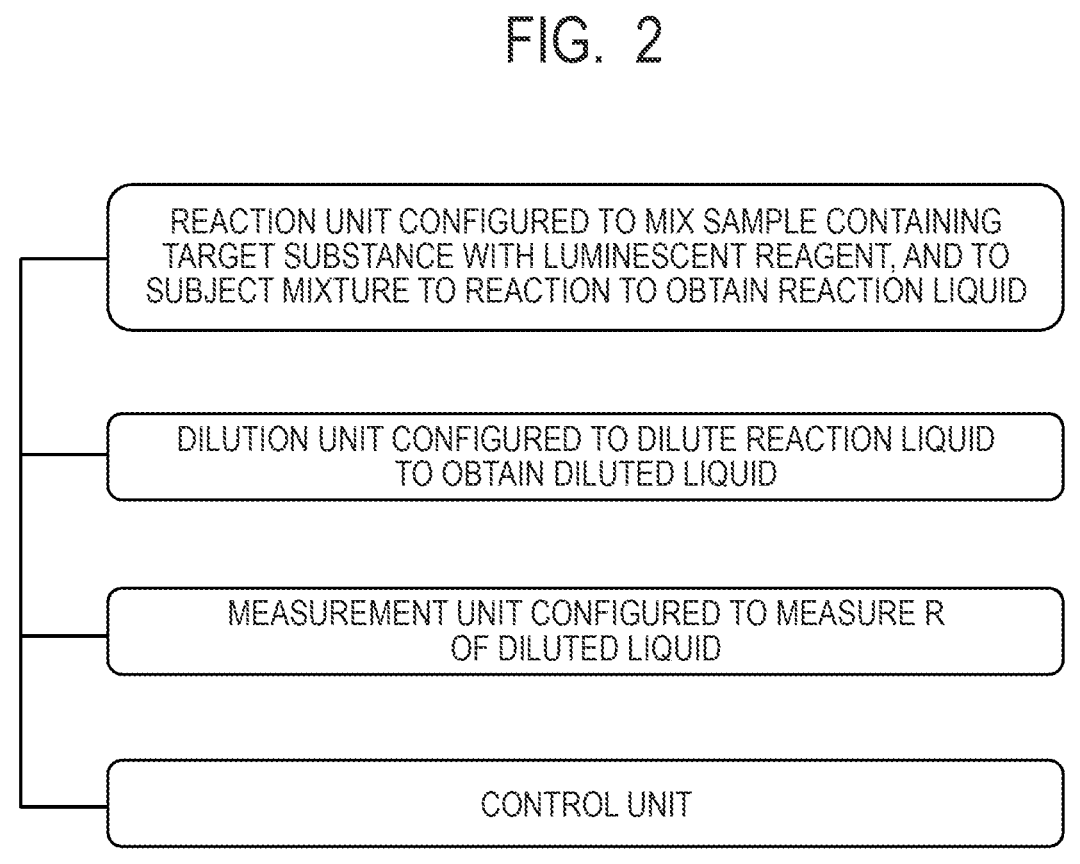

REACTION UNIT CONFIGURED TO MIX SAMPLE CONTAINING TARGET SUBSTANCE WITH LUMINESCENT REAGENT, AND TO SUBJECT MIXTURE TO REACTION TO OBTAIN REACTION LIQUID

DILUTION UNIT CONFIGURED TO DILUTE REACTION LIQUID TO OBTAIN DILUTED LIQUID

MEASUREMENT UNIT CONFIGURED TO MEASURE R OF DILUTED LIQUID

CONTROL UNIT

METHOD ANALYSIS EMPLOYING MEASUREMENT BASED ON POLARIZATION ANISOTROPY

BACKGROUND OF THE INVENTION

Field of the Invention

The present invention relates to an analysis method and an analysis apparatus each employing measurement based on polarization anisotropy.

Description of the Related Art

In the fields of medicine and clinical tests, high-sensitivity detection or quantification of a trace amount of a biological component from, for example, blood or a collected part of an organ is required for investigating, for example, the cause and presence or absence of a disease.

Among test techniques for biological components, immunoassays are widely utilized. In many of the immunoassays, a washing step called bound/free (B/F) separation is required. As an immunoassay that does not require the B/F separation, there is known a latex agglutination method utilizing an antigen-antibody reaction. In the latex agglutination method, latex particles each having supported thereon, for example, an antibody that specifically binds to a target substance are mixed with a liquid that may contain the target substance, and the degree of agglutination of the latex particles is measured.

In the latex agglutination method, the target substance is captured by the antibody bound to the latex particles and specific to the target substance, and a plurality of the latex particles are crosslinked via the captured target substance, with the result that the agglutination of the latex particles occurs. That is, the amount of the target substance in a liquid sample such as a biological sample can be quantified by evaluating the degree of the agglutination of the latex particles. The degree of the agglutination can be quantified by measuring and evaluating a change in amount of light transmitted through or scattered by the liquid sample.

The latex agglutination method can detect/quantitatively evaluate an antigen as the target substance in a simple and rapid manner, but has involved a problem with detection limits in that the antigen cannot be detected when its amount in the liquid sample such as the biological sample is small.

In order to improve detection sensitivity for the target substance, it is required that the degree of the agglutination be measured with higher sensitivity. That is, it is conceivable to replace a system for measuring the change in amount of the light transmitted through or scattered by the liquid sample with a method for detection/quantification utilizing a luminescence characteristic with higher sensitivity. Specifically, there has been proposed, for example, a specimen test method utilizing a fluorescence depolarization measurement (Japanese Patent Publication No. H03-52575 and Japanese Patent No. 2893772).

In Japanese Patent Publication No. H03-52575, it is proposed that an apparatus for the fluorescence depolarization measurement be improved to be clinically used.

In the fluorescence depolarization measurement, the B/F separation required in a general fluorescence measurement method is not required.

Accordingly, use of the fluorescence depolarization measurement enables a simple specimen test as with the latex agglutination method. Further, it is conceived that use of the fluorescence depolarization measurement enables measurement by the same test system as in the latex agglutination method by merely mixing a luminescent substance that specifically reacts with the target substance in a measurement process. Meanwhile, in Japanese Patent Publication No. H03-52575, there is a proposal of use of a single molecule such as fluorescein as a luminescent material, which is applicable only to a drug, a low-molecular-weight antigen, and the like in principle.

Japanese Patent No. 2893772 has solved the problem of Japanese Patent Publication No. H03-52575, i.e., the problem in that the fluorescence depolarization measurement is applied only to a drug, a low-molecular-weight antigen, and the like. That is, in Japanese Patent No. 2893772, with an aim to apply the fluorescence depolarization measurement to a macromolecule such as a protein, it is proposed to use, as a luminescent material, a material obtained by adsorbing a dye having a long-lifetime luminescence characteristic onto latex particles. In Japanese Patent No. 2893772, it is proposed that a high-molecular-weight substance be quantified by balancing a reduction in rotational Brownian motion of the substance in a liquid due to an increase in particle diameter and the length of emission lifetime based on the principle of the fluorescence depolarization measurement. However, in Japanese Patent No. 2893772, a fluorescent substance is supported on the latex particles after synthesis of the particles, and hence an interaction between fluorescent substances adsorbed in the vicinity of surfaces of the particles or the like makes it difficult to stably determine the polarization anisotropic property of the testing particles. Further, in Japanese Patent No. 2893772, bovine serum albumin (BSA), which is a biomolecule, is supported on surfaces of the particles in order to suppress nonspecific adsorption, and hence there is a risk in that a lot-to-lot variation may occur owing to a broad particle size distribution and BSA, which is a protein. Accordingly, measurement is performed with the concentration of the target substance being on the order of $\mu$g/mL, which is not greatly different from the latex method in terms of measurement sensitivity.

In measurement based on the fluorescence depolarization measurement, it is important that the reaction between the target substance and the luminescent substance be sufficiently performed. However, the reaction takes time in some cases such as a case in which affinity between the target substance and the luminescent substance is weak. In measurement using the fluorescence depolarization measurement, there has been a problem of performing the measurement within as short a period of time as possible and with high sensitivity.

SUMMARY OF THE INVENTION

According to one embodiment of the present invention, there is provided an analysis method including measuring a value (R) for polarization anisotropy through use of a luminescent reagent that reacts with a target substance, to thereby determine at least any one of the presence or absence of the target substance and a concentration of the target substance, the analysis method including: a reaction step including mixing a sample containing the target substance with the luminescent reagent, and subjecting the mixture to a reaction to obtain a reaction liquid; a dilution step of diluting the reaction liquid to obtain a diluted liquid; and a measurement step of measuring the R of the diluted liquid, the luminescent reagent including luminescent particles.

In addition, according to one embodiment of the present invention, there is provided an analysis apparatus for measuring a value (R) for polarization anisotropy through use of a luminescent reagent that reacts with a target substance, to thereby measure at least any one of the presence or absence of the target substance and a concentration of the target substance, the analysis apparatus including: a reaction unit configured to mix a sample containing the target substance with the luminescent reagent, and to subject the mixture to a reaction to obtain a reaction liquid; a dilution unit configured to dilute the reaction liquid to obtain a diluted liquid; a measurement unit configured to measure the R of the diluted liquid; and a control unit, the luminescent reagent including luminescent particles.

Further features of the present invention will become apparent from the following description of exemplary embodiments with reference to the attached drawings.

BRIEF DESCRIPTION OF THE DRAWINGS

FIG. 2 is a schematic view for illustrating an apparatus according to an embodiment of the present invention.

DESCRIPTION OF THE EMBODIMENTS

Figure 1:
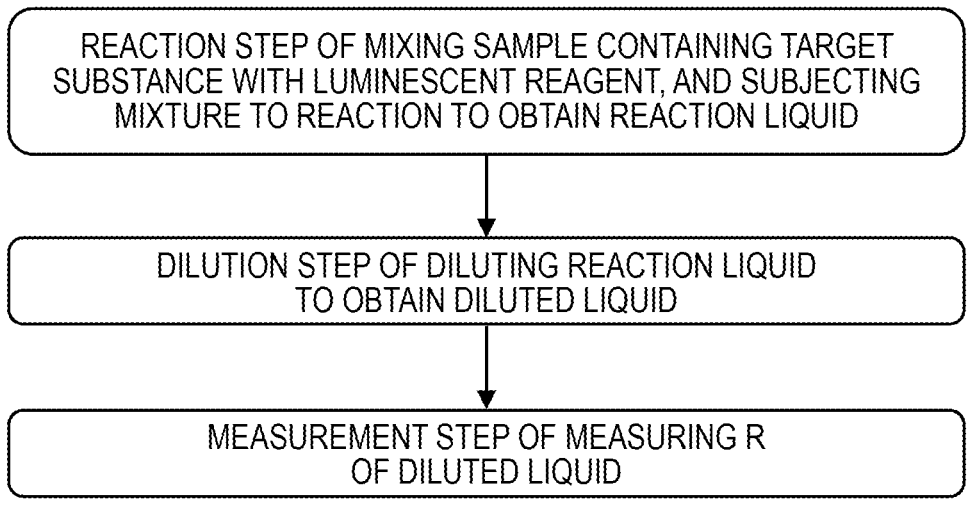
FIG. 1 is a schematic view for illustrating an analysis method according to an embodiment of the present invention.

Exemplary embodiments of the present invention are described in detail below. However, the embodiments are not intended to limit the scope of the present invention.

According to one embodiment of the present invention, there is provided the following analysis method: an analysis method including measuring a value (R) for polarization anisotropy through use of a luminescent reagent that reacts with a target substance, to thereby determine at least any one of the presence or absence of the target substance and a concentration of the target substance, the analysis method including a reaction step including mixing a sample containing the target substance with the luminescent reagent, and subjecting the mixture to a reaction to obtain a reaction liquid; a dilution step of diluting the reaction liquid to obtain a diluted liquid; and a measurement step of measuring the R of the diluted liquid, the luminescent reagent including luminescent particles.

The analysis method according to this embodiment solves the problem of performing measurement based on polarization anisotropy in which the reaction between the target substance and the luminescent reagent is performed within a short period of time, and in which high-sensitivity measurement can be performed. The reaction between the target substance and the luminescent reagent may be exemplified by binding between the target substance and a substance (e.g., a ligand to be described later) capable of binding with the target substance out of substances included in the luminescent reagent.

The inventors have focused their attention on the fact that, in order to shorten a reaction time, particularly in, for example, the case in which the amount of the target substance is small, or the case in which affinity between the target substance and the luminescent reagent is low, it is preferred to subject the sample containing the target substance and the luminescent reagent to the reaction under a state of being as concentrated as possible.

Now, when the luminescent reagent includes a plurality of luminescent particles each containing a fluorescent substance, a fluorescence intensity is increased, and hence a change in value (R) based on polarization anisotropy can be grasped as a large one, to thereby enable high-sensitivity measurement.

Meanwhile, when the concentration of the luminescent particles is high during the measurement of the R, multiple scattering occurs, and hence the change in R cannot be grasped as a large one. That is, when multiple scattering occurs, the R becomes high even for particles that have not reacted with the target substance and have not aggregated, and hence it is difficult to grasp the change in R before and after the reaction with the target substance.

The inventors have found that, when the target substance and the luminescent reagent are concentrated in the above-mentioned reaction step, and then undergo the dilution step, there can be realized an analysis method based on polarization anisotropy with a short reaction time and high sensitivity.

That is, an object of the present invention is to provide an analysis method and an analysis apparatus each of which is capable of determining at least any one of the presence or absence of the target substance and the concentration of the target substance based on polarization anisotropy within a short period of time and with high sensitivity by the above-mentioned analysis method according to this embodiment.

(Value for Polarization Anisotropy)

In this embodiment, the value for polarization anisotropy (sometimes referred to as R) is defined as described below. That is, the R is a value showing a relationship between the luminescence intensity of a polarized light component in a parallel direction to radiated polarized light and the luminescence intensity of a polarized light component in a perpendicular direction thereto regarding luminescence generated by exciting a luminescent substance through irradiation with polarized light. More specifically, the R is a value calculated from the luminescence intensity of a luminescence component having a vibration direction parallel to that of given polarized light, the luminescence intensity being determined when the luminescent substance is excited by the polarized light. Further, the R is a value indicating the ratio of a difference between the luminescence intensity of a luminescence component having a vibration direction parallel to that of a first polarized light beam at the time of excitation by the first polarized light beam and the luminescence intensity of a luminescence component having a vibration direction orthogonal to that of the first polarized light beam at the time of excitation by the first polarized light beam to the sum of the luminescence intensities. The R may be corrected with: a ratio between the luminescence intensity of a luminescence component having a vibration direction orthogonal to that of a second polarized light beam having a vibration direction orthogonal to that of the first polarized light beam at the time of excitation by the second polarized light beam and the luminescence intensity of a luminescence component having a vibration direction parallel to that of the second polarized light beam having a vibration direction orthogonal to that of the first polarized light beam at the time of excitation by the second polarized light beam; and other constants. The value for polarization anisotropy encompasses values referred to as "polarization anisotropic property", "degree of polarization", and the like.

More specifically, for example, the R may be "r" in the following equation (1):

$$r = \frac{I_{VV} - G * I_{VH}}{I_{VV} + 2 * G * I_{VH}} \qquad \text{Equation (1)}$$

$$G = \frac{I_{HV}}{I_{HH}}$$

in the equation (1), $I_{VV}$ represents the luminescence intensity of a luminescence component having a vibration direction parallel to that of a first polarized light beam at the time of excitation by the first polarized light beam, $I_{VH}$ represents the luminescence intensity of a luminescence component having a vibration direction orthogonal to that of the first polarized light beam at the time of excitation by the first polarized light beam, $I_{HV}$ represents the luminescence intensity of a luminescence component having a vibration direction orthogonal to that of a second polarized light beam having a vibration direction orthogonal to that of the first polarized light beam at the time of excitation by the second polarized light beam, $I_{HH}$ represents the luminescence intensity of a luminescence component having a vibration direction parallel to that of the second polarized light beam having a vibration direction orthogonal to that of the first polarized light beam at the time of excitation by the second polarized light beam, and G represents a correction value.

In addition, the R may be r' in the following equation (2).

$$r' = \frac{I_{VV} - G * I_{VH}}{I_{VV} + G * I_{VH}} \qquad \text{Equation (2)}$$

$$G = \frac{I_{HV}}{I_{HH}}$$

Each symbol is the same as that in the equation (1).

With regard to conditions for the measurement of the R, for example, it is preferred that the measurement be performed in a liquid having a temperature of from 0° C. to 50° C., and the viscosity of the liquid be 0.5 mPa·s or more and 50 mPa·s or less. When the luminescent reagent is particles each containing a europium complex, the measurement is preferably performed with the concentration of the luminescent reagent being 0.001 mg/ml or more and 0.1 mg/ml or less, and a measurement wavelength (an excitation wavelength) is preferably 500 nm or more and 700 nm or less.

In addition, R0, which represents the R measured for the luminescent reagent that has not been mixed with the target substance, preferably satisfies R0≥0.001.

(With Regard to Reaction Step)

For each step, reference may be made to FIG. 1. In the reaction step, a sample containing the target substance and the luminescent reagent are mixed to provide a mixed liquid, and the target substance and the luminescent reagent are subjected to a reaction. The mixed liquid is a liquid containing the luminescent reagent and the target substance, and may further contain an additive or the like in addition to the foregoing. The reaction is preferably performed at a pH in the range of from 3.0 or more to 11.0 or less. In addition, a mixing temperature falls within the range of from 20° C. or more to 50° C. or less. A reaction time is set in view of the concentration of the target substance in the sample, the affinity between the target substance and the luminescent reagent, and the like, but is preferably 5 minutes or more and 24 hours or less, more preferably 5 minutes or more and 1 hour or less. The target substance and the luminescent reagent are described later.

(With Regard to Dilution Step)

In the dilution step, the reaction liquid is diluted to obtain a diluted liquid. The dilution step is performed after the reaction step. By virtue of providing the dilution step, the luminescent reagent and the target substance can be subjected to the reaction at sufficiently high concentrations, and hence a sufficient reaction can be performed within a short period of time. A reaction rate between the target substance and the ligand is determined by a binding constant therebetween, and the binding constant is dependent on the diffusion constants of the target substance and the ligand. Accordingly, when the concentration of any one of the target substance or the ligand in a reaction system is low, the reaction rate also becomes slow. Besides, for example, an antigen-antibody reaction is, in many cases, an equilibrium reaction with a dissociation rate constant slower than a binding rate, but once binding occurs, dissociation does not occur easily. In view of this, the analysis method according to this embodiment, in which the concentrations of the target substance and the ligand in the system are kept high at the time when the reaction is caused, and the reaction liquid is diluted at the time of the measurement, is effective.

In the analysis method according to this embodiment, the luminescent reagent includes the luminescent particles, and hence its effect is strongly exhibited. When the luminescent reagent includes the luminescent particles, a change in anisotropic property of polarized luminescence can be detected with high sensitivity in correspondence to the aggregation/dispersion behavior of the particles. That is, when the luminescent reagent is particles, the change in R can be grasped as a large one, to thereby enable high-sensitivity measurement. Meanwhile, when the concentration of the luminescent reagent is high during the measurement of the R, multiple scattering occurs, and hence the change in R cannot be grasped as a large one.

That is, when multiple scattering occurs, R0, which represents the R in the case of subjecting particles that have not reacted with the target substance and have not aggregated to the measurement, is increased, and hence it is difficult to grasp the change in R before and after the reaction with the target substance. However, when the concentration of the luminescent reagent is low at the time of the reaction, the reaction between the target substance and the luminescent reagent takes time. When dilution is performed after the reaction, while multiple scattering at the time of the measurement is suppressed, the concentration of the luminescent reagent can be set to be high in the reaction step, and hence the reaction time can be shortened. In addition, when the viscosity of the solution at the time of the measurement is excessively high, R0 is increased, and hence the change in R cannot be grasped as a large one. This problem is also eliminated by providing the dilution step.

Meanwhile, when the R of a liquid containing particles at a high concentration is measured, a polarized light component of luminescence is eliminated owing to the influence of scattering by the particles, resulting in a high R even in the case in which the target substance is not present. Accordingly, the measurement needs to be performed with the reaction liquid appropriately diluted through the dilution step. In addition, the viscosity of the measurement object during the measurement of the R significantly influences the R, but when the viscosity takes a constant value through the dilution in the dilution step, the R becomes stable.

A dilution factor is not particularly specified as long as the measurement of the R can be sufficiently performed, but is preferably 2-fold or more, more preferably 2-fold or more and 1,000-fold or less, still more preferably 10-fold or more and 100-fold or less. Alternatively, the dilution is preferably performed so as to achieve a concentration of the luminescent reagent of 0.05 mg/ml or less. In addition, the dilution is preferably performed so as to achieve a viscosity of 25 mPa·s or less, more preferably 2.5 mPa·s or less.

(With Regard to Measurement Step)

In the measurement step, the R of the reaction liquid is measured. With regard to conditions for the measurement, for example, it is preferred that the measurement be performed in a liquid having a temperature of from 0° C. to 50° C., and the viscosity of the liquid be 0.5 mPa·s or more and 50 mPa·s or less. The measurement is preferably performed with the concentration of the luminescent reagent being 0.001 mg/ml or more and 0.1 mg/ml or less, and a measurement wavelength (an excitation wavelength) is preferably 500 nm or more and 700 nm or less. In order to suppress the influence of multiple scattering, the optical path of an optical system may be shortened. For example, the optical path, which is generally set to 10 mm in many cases, may be set to 5 mm or less.

(Target Substance)

Examples of the target substance may include an antigen, an antibody, a low-molecular-weight compound, various receptors, an enzyme, a substrate, a nucleic acid, a cytokine, a hormone, a neurotransmitter, a transmitter, and a membrane protein. Examples of the antigen include an allergen, a bacterium, a virus, a cell, a cell membrane constituent, a cancer marker, various disease markers, an antibody, a blood-derived substance, a food-derived substance, a natural product-derived substance, and any low-molecular-weight compound. Examples of the nucleic acid include DNA, RNA, or cDNA derived from a bacterium, a virus, or a cell, a part or fragment thereof, a synthetic nucleic acid, a primer, and a probe. Examples of the low-molecular-weight compound include a cytokine, a hormone, a neurotransmitter, a transmitter, a membrane protein, and a receptor therefor. At least any one of the presence or absence of any such target substance and the concentration of the target substance may be determined by the analysis method according to this embodiment. The presence or absence of the target substance may be determined by comparing the concentration of the target substance to a predetermined threshold. For example, the target substance may be determined to be present when the concentration of the target substance is equal to or higher than the predetermined threshold, and to be absent when the concentration is lower than the predetermined threshold.

(Luminescent Reagent)

In this embodiment, the luminescent reagent is a reagent that produces luminescence, in particular, a reagent that is excited to emit light when irradiated with light, and excludes a reagent based on luminescence produced through a chemical reaction like luminol. The luminescence encompasses phosphorescence and fluorescence, but is preferably phosphorescence. In this embodiment, the luminescent reagent more preferably includes a europium complex. In addition, in this embodiment, the luminescent reagent more preferably includes particles. In this embodiment, the luminescent reagent most preferably includes particles each containing a europium complex. In addition, the luminescent reagent preferably includes a ligand specific to the target substance. By including the ligand, the luminescent reagent of this embodiment enables detection/quantification of the target substance based on polarization anisotropy. In this embodiment, the "ligand" refers to a compound that specifically binds to a particular target substance.

Any compound that shows affinity for a particular substance may be used as the ligand. Examples of the ligand and the target substance, or a combination of the target substance and the ligand may include the following. That is, the examples may include: an antigen and an antibody; a low-molecular-weight compound and a receptor therefor; an enzyme and a substrate; and nucleic acids complementary to each other. Further, the examples may include an antibody and any of the following substances specific thereto: an allergen, a bacterium, a virus, a cell, a cell membrane constituent, a cancer marker, various disease markers, an antibody, a blood-derived substance, a food-derived substance, a natural product-derived substance, and any low-molecular-weight compound. Further, the examples may include a receptor and any of the following substances specific thereto: a low-molecular-weight compound, a cytokine, a hormone, a neurotransmitter, a transmitter, and a membrane protein. Further, the examples may include DNA, RNA, or cDNA derived from a bacterium, a virus, or a cell, a part or fragment thereof, a synthetic nucleic acid, a primer, or a probe, and a nucleic acid having complementarity thereto. Other than the foregoing, any combination known to have affinity may be used as the combination of the target substance and the ligand. A typical example of the ligand in this embodiment is any one of an antibody, an antigen, and a nucleic acid. In addition, a particularly preferred example of the combination of the target substance and the ligand is a combination of an antigen and an antibody, whose effect is clearly demonstrated in Examples described below.

Figure 3:
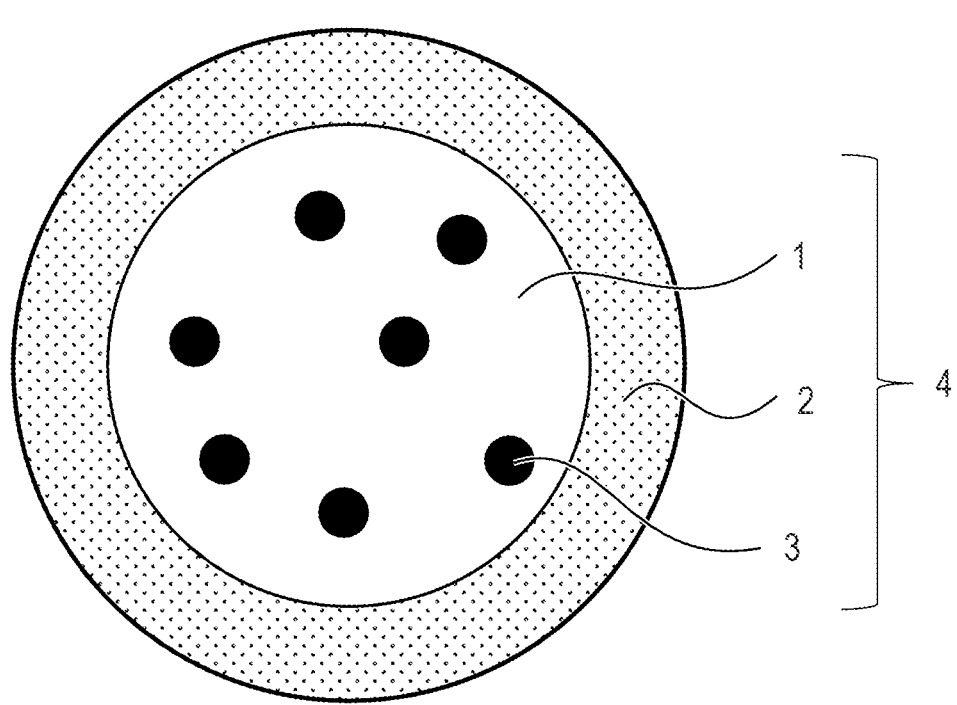
FIG. 3 is a schematic view for illustrating a luminescent reagent to be used in the embodiments of the present invention.

FIG. 3 is a schematic view for illustrating an example of the luminescent reagent to be used in this embodiment. A luminescent reagent 4 to be used in this embodiment includes, for example, a particle substrate 1 containing europium complexes 3 as luminescent molecules. Further, the luminescent reagent 4 may include a hydrophilic layer 2 coating the surface thereof. The diameter of the particle in FIG. 3 is 25 nm or more and 500 nm or less.

The diameter of each of the particles may be determined by a dynamic light scattering method. When particles dispersed in a solution are irradiated with laser light and the resultant scattered light is observed with a photon detector, an intensity distribution due to interference of the scattered light is constantly fluctuating because the particles are constantly shifting their positions by Brownian motion.

The dynamic light scattering method is a measurement method for observing the state of the Brownian motion as a fluctuation in scattered light intensity. The fluctuation of scattered light with respect to time is expressed as an autocorrelation function, and a translational diffusion coefficient is determined. A Stokes diameter is determined from the determined diffusion coefficient, and the size of each of the particles dispersed in the solution can be derived.

The luminescent reagent desirably has nothing provided on the surfaces of its particles from the viewpoint of keeping the uniformity and monodispersity of the particles. However, for the purpose of use in the analysis method according to this embodiment, nonspecific adsorption of substances other than the target onto the particles needs to be prevented, and hence the luminescent reagent preferably includes the hydrophilic layer for keeping its surface hydrophilic.

A method involving supporting BSA on the surface of each of the particles is widely used as a technique for keeping hydrophilicity, but this method may cause a lot of variation. In view of this, the luminescent reagent preferably includes a hydrophilic layer formed of a hydrophilic polymer. The concentration of the luminescent reagent in the mixed liquid is preferably from 0.000001 mass % to 1 mass %, more preferably from 0.00001 mass % to 0.001 mass %.

The luminescent reagent to be used in this embodiment can emit light having a long lifetime by virtue of containing the europium complex. In the luminescent reagent to be used in this embodiment, an average particle diameter that is the average of the diameters of the particles is preferably 25 nm or more and 500 nm or less, and the average particle diameter is more preferably 50 nm or more and 300 nm or less. When the average particle diameter is more than 500 nm, the R (R0) before aggregation becomes high, resulting in a small difference from the R after the aggregation reaction. In addition, when the average particle diameter is less than 25 nm, a change between sizes before and after the aggregation becomes small to make it difficult to grasp the change of the R through luminescence depolarization.

By reducing the particle size distribution of the luminescent reagent and introducing the europium complex as the luminescent molecule, a change in polarized luminescence characteristic can be grasped even when the dispersion state of the particles in the liquid undergoes a slight change. Specifically, even if the concentration of the target substance in the solution is from about a nanogram to about a picogram, for example, 1 picogram or more and 10 picograms or less, per mL, when the luminescent reagent aggregates via the target substance, a change in rotational Brownian motion of the luminescent reagent can be grasped as a change in polarization anisotropy.

The "polarized luminescence" refers to the following phenomenon: when a luminescent material having an anisotropic property in transition moment (transition dipole moment) uses polarized light along its transition moment as excitation light, its luminescence is also polarized light along the transition moment. The europium complex shows fluorescent luminescence based on energy transfer from the ligand to the central metal ion, and hence the transition moment is complicated, but red luminescence around 610 nm, which is derived from electronic transition from the lowest excited state 5D0 to 7F2, is emitted as polarized light.

The principle of polarization anisotropy is the measurement of a shift in transition moment due to the rotational motion of a luminescent material during the occurrence of polarized luminescence. The rotational motion of the luminescent material may be expressed by the equation (3):

$$Q = 3V\eta/kT \qquad (3)$$

where Q represents the rotational relaxation time of the material, V represents the volume of the material, η represents the viscosity of a solvent, k represents the Boltzmann constant, and T represents an absolute temperature.

The rotational relaxation time of the material is a period of time required for a molecule to rotate by an angle θ(68.5°) at which cos θ=1/e.

It is found from the equation (3) that the rotational relaxation time of the luminescent material is proportional to the volume of the material, that is, when the luminescent material has a particulate shape, the cube of the particle diameter. Meanwhile, a relationship between the emission lifetime of the luminescent material and the degree of polarization serving as the value for polarization anisotropy may be expressed by the equation (4):

$$p0/p = 1 + A(\tau/Q) \qquad (4)$$

where p0 represents a degree of polarization at a time when the material is stationary (Q=∞), "p" represents the degree of polarization, A is a constant, τ represents the emission lifetime of the material, and Q represents the rotational relaxation time.

It is found from the equation (3) and the equation (4) that the degree of polarization is influenced by the emission lifetime of the luminescent material and the rotational relaxation time, that is, the volume (particle diameter) of the luminescent material, i.e., influenced by the balance between the particle diameter and emission lifetime of the luminescent material.

When the degree of polarization of the luminescent material represented by the equation (4) is determined experimentally, it is appropriate that polarized light be allowed to enter the luminescent material, and luminescence be detected in a 90° direction with respect to the traveling direction and vibration direction of excitation light. In this case, it is appropriate that the detected light be detected by being divided into polarized light components in parallel and perpendicular directions with respect to the polarized light that is the incident light, and for example, a polarization anisotropic property represented by the equation (5) be adopted as the value for polarization anisotropy:

$$r(t) = (I//(t) - GI\perp(t)/(I//(t) + 2GI\perp(t) \qquad (5)$$

where r(t) represents a polarization anisotropic property at a time "t", I//(t) represents the luminescence intensity of a luminescence component parallel to the excitation light at the time "t", I⊥(t) represents the luminescence intensity of a luminescence component perpendicular to the excitation light at the time "t", and G represents a correction value, the ratio of I⊥/I// measured with excitation light having a vibration direction different by 90° from that of the excitation light used for sample measurement.

That is, when the particle size and the emission lifetime fall within appropriate ranges, a change in size of the luminescent material due to, for example, a reaction with the target substance can be sensitively read as a change in polarization anisotropic property. That is, the r(t) of the unaggregated luminescent material is observed to be low, and the r(t) of the aggregated luminescent material is observed to be high. This is the principle of polarization anisotropy.

The value for polarization anisotropy may be corrected with G and 2G, or may be a value without G and 2G.

(Particle Substrate 1)

The shapes of the luminescent reagent 4 and the particle substrate 1 to be used in this embodiment are not limited. The particle substrate 1 is not particularly specified as long as the particle substrate 1 is a material capable of stably incorporating the europium complex, but is preferably a polymer containing a styrene unit and an organic silane unit. In particular, for example, a polymer obtained by polymerizing a composition containing styrene as a main component and a radically polymerizable organic silane is suitably used. When the composition contains styrene as the main component, particles having an extremely uniform particle size distribution can be produced by an emulsion polymerization method to be described later. In addition, when a polymer containing an organic silane unit is adopted, a silanol group (Si—OH) is produced in the polymer in an aqueous solvent, and particle substrate surfaces form a siloxane bond (Si—

O—Si) to each other, via which the hydrophilic layer to be described later or a ligand can be provided. The particles according to this embodiment each preferably have a ligand-bonding functional group capable of bonding a ligand to the outside of the particle substrate.

(Hydrophilic Layer 2)

The hydrophilic layer 2 may be formed by incorporating a hydrophilic polymer or a hydrophilic molecule on the outside of the particle substrate 1. The hydrophilic polymer or the hydrophilic molecule is a polymer or molecule containing a hydrophilic group, and specific examples of the hydrophilic group include molecules or polymers each having a hydroxy group, an ether, pyrrolidone, or a betaine structure. Specific examples of the hydrophilic polymer include polyethylene glycol, polyvinylpyrrolidone, a polymer of sulfobetaine, a polymer of phosphobetaine, and polyglycidyl methacrylate whose molecule has an end modified with a hydroxy group by ring-opening a glycidyl group, and those hydrophilic polymers may each be used as a main component of the hydrophilic layer 2. Alternatively, the hydrophilic layer 2 may be formed by directly providing a single molecule having a hydrophilic group on the surface of the particle substrate 1 through use of a silane coupling agent or the like. The thickness of the hydrophilic layer 2 is not limited, but does not need to be set to be large beyond a thickness with which hydrophilicity can be exhibited. When the hydrophilic layer 2 is excessively thick, there is a risk in that the hydrophilic layer may become hydrogel-like and be hydrated by the influence of ions in the solvent, to thereby make its thickness unstable. The thickness of the hydrophilic layer 2 is suitably 1 nm or more and 15 nm or less.

(Europium Complex 3)

The luminescent reagent to be used in this embodiment may include the europium complex 3 as a luminescent dye. The europium complex 3 has a feature in that the wavelength and intensity of its luminescence are hardly influenced by the surroundings, and hence the luminescence has a long lifetime. The europium complex 3 is made up of a europium element and a ligand. In consideration of the emission lifetime, a visible emission wavelength region, and the like, the luminescent dye is preferably a europium complex. Europium generally has an emission lifetime of 0.1 ms or more and 1.0 ms or less. The emission lifetime and the rotational relaxation time obtained from the equation (1) need to be appropriately adjusted. In the case of europium in a water dispersion, when the diameter of the luminescent reagent is 50 nm or more and 300 nm or less, the R significantly changes before and after aggregation.

At least one of the constituent ligands of the europium complex 3 is a ligand having a light-collecting function. The "light-collecting function" refers to an action of being excited at a particular wavelength to excite the central metal of the complex through energy transfer. In addition, it is preferred that the constituent ligands of the europium complex 3 include a ligand such as a β-diketone to prevent coordination of a water molecule. The ligand such as the β-diketone coordinated to a europium ion suppresses a deactivation process due to the transfer of energy to a solvent molecule or the like to provide strong fluorescent luminescence.

The europium complex 3 may be a polynuclear complex.

In addition, specific examples of the europium complex include [tris(2-thenoyltrifluoroacetone)(bis(triphenylphosphineoxide))europium(III)], [tris(2-thenoyltrifluoroacetone)(triphenylphosphineoxide)(dibenzylsulfoxide)europium (III)], and [tris(2-thenoyltrifluoroacetone)(phenanthroline)europium(III)].

At the time of a state in which the Brownian rotational motion of the europium complex 3 can be regarded as stationary in a medium, the R expressed by the equation (3) is desirably 0.08 or more. The state in which the Brownian rotational motion can be regarded as stationary refers to a state in which the rotational relaxation time of the particles is sufficiently longer than the emission lifetime of the europium complex 3.

The europium complex 3 is preferably incorporated in a larger amount into the particle substrate 1 because a luminescence intensity per particle becomes stronger. Meanwhile, when the europium complexes 3 aggregate in the particle substrate 1, an interaction between ligands influences the excitation efficiency of the europium complex 3 and the like to make it difficult to measure the R while keeping reproducibility. Whether the europium complex 3 shows non-aggregated luminescence behavior in the particle substrate 1 may be judged from an excitation spectrum of the sample.

Particles having strong luminescence not only enable high-sensitivity measurement, but also enable an increase in biochemical reaction rate because luminescence is kept even when their particle diameters are reduced. As the particle diameters become smaller, the diffusion coefficient of Brownian motion in the liquid becomes larger, and hence the reaction can be detected in a shorter period of time.

When a liquid having such particles dispersed therein is used for the analysis method according to this embodiment, a change in anisotropic property of polarized luminescence can be detected with high sensitivity in correspondence to the aggregation/dispersion behavior of the particles. A dispersion obtained by dispersing such particles in an aqueous solvent can be utilized as a high-sensitivity test reagent making use of polarization anisotropy. A buffer solution may be used as the aqueous solvent. In addition, a surfactant, a preservative, a sensitizer, or the like may be added into the aqueous solvent in order to enhance the stability of the liquid having the particles dispersed therein.

(Method of Producing Luminescent Reagent)

Next, an example of a method of producing the luminescent reagent to be used in this embodiment is described.

The method of producing the luminescent reagent includes a step (first step) of mixing radically polymerizable monomers including at least styrene and a radically polymerizable organic silane, a radical initiator, a polarized luminescent europium complex, and a hydrophilic polymer with an aqueous medium to prepare an emulsion.

Further, the method of producing the luminescent reagent includes a step (second step) of heating the emulsion to polymerize the radically polymerizable monomers.

The method of producing the luminescent reagent may include a step (third step) of providing a ligand-bonding functional group to be described later on the surface of the luminescent reagent. Herein, the ligand-bonding functional group refers to a functional group that can bond a ligand. Specifically, any one of a carboxy group, an amino group, a thiol group, an epoxy group, a maleimide group, a succinimidyl group, or an alkoxysilyl group (silicon alkoxide structure) may be used.

(Radically Polymerizable Monomers)

The production of the luminescent reagent is performed by polymerizing radically polymerizable monomers, and the radically polymerizable monomers include at least styrene and a radically polymerizable organic silane. The radically polymerizable monomers may further include a monomer selected from the group consisting of: an acrylate-based monomer; and a methacrylate-based monomer. Examples of the monomer may include butadiene, vinyl acetate, vinyl chloride, acrylonitrile, methyl methacrylate, methacrylonitrile, methyl acrylate, and mixtures thereof. That is, one kind or a plurality of kinds of those monomers may be used in addition to styrene and the radically polymerizable organic silane. In addition, a monomer having two or more double bonds per molecule, such as divinylbenzene, may be used as a crosslinking agent.

The inclusion of the radically polymerizable organic silane in the radically polymerizable monomers provides a siloxane bond on the particle substrate 1. Examples of the radically polymerizable organic silane may include vinyltrimethoxysilane, vinyltriethoxysilane, p-styryltrimethoxysilane, 3-methacryloxypropylmethyldimethoxysilane, 3-methacryloxypropyltrimethoxysilane, 3-methacryloxypropylmethyldiethoxysilane, 3-methacryloxypropyltriethoxysilane, 3-acryloxypropyltrimethoxysilane, and combinations thereof. The use of the radically polymerizable organic silane serves to form a backbone of an inorganic oxide in the particle substrate 1 to improve the physical and chemical stability of the luminescent reagent. Further, the use of the radically polymerizable organic silane enhances affinity between the particle substrate 1 and each of the hydrophilic layer 2 and the ligand-bonding functional group.

Further, the inclusion of the radically polymerizable organic silane in the radically polymerizable monomers provides a silanol group on the surface of the particle substrate 1. The silanol group and the hydrophilic polymer such as PVP form a hydrogen bond. Thus, the hydrophilic polymer such as PVP is more strongly adsorbed onto the surface of the particle substrate 1.

(Radical Initiator)

A wide range of compounds selected from, for example, azo compounds and organic peroxides may each be used as the radical initiator. Specific examples thereof may include 2,2'-azobis(isobutyronitrile), 2,2'-azobis(2,4-dimethylvaleronitrile), 2,2'-azobis(2-methylbutyronitrile), 4,4'-azobis(4-cyanovaleric acid), 2,2'-azobis(2-methylpropionamidine) dihydrochloride, dimethyl 2,2'-azobis(2-methylpropionate), tert-butyl hydroperoxide, benzoyl peroxide, ammonium persulfate (APS), sodium persulfate (NPS), and potassium persulfate (KPS).

(Hydrophilic Polymer)

The luminescent reagent may include a hydrophilic polymer as the hydrophilic layer. The hydrophilic polymer preferably suppresses nonspecific adsorption. Examples of the hydrophilic polymer include hydrophilic polymers each containing a unit having an ether, a betaine, or a pyrrolidone ring. It is preferred that the hydrophilic layer be included in the synthesized luminescent reagent, and be mainly present on the particle surface on the outside of the particle substrate. Herein, a polymer having a pyrrolidone ring is sometimes abbreviated as "PVP". When the PVP is fed at the time of the synthesis of the luminescent reagent, a nonspecific adsorption-suppressing ability and a ligand-bonding ability can be simultaneously provided for the luminescent reagent. The PVP to be fed at the time of the synthesis has higher hydrophilicity than the radically polymerizable monomers, and hence is present at an interface between the solvent and the particle substrate that is being polymerized at the time of the synthesis. The particle substrate adsorbs the PVP onto the outside thereof by involving part of the PVP at the time of the polymerization, or by physical/chemical adsorption such as an interaction between a pyrrolidone ring and styrene (radically polymerizable monomer).

The molecular weight of the PVP is preferably 10,000 or more and 100,000 or less, more suitably 40,000 or more and 70,000 or less. When the molecular weight is less than 10,000, the hydrophilicity of the surface of the luminescent reagent is weak, and hence nonspecific adsorption is liable to occur. When the molecular weight is more than 100,000, the hydrophilic layer becomes so thick as to gel, thereby becoming difficult to handle.

In addition to the PVP, another hydrophilic polymer may be added as a protective colloid at the time of the synthesis of the particle substrate.

In addition, the luminescent reagent preferably satisfies A2-A1≤0.1.

A1 and A2 are defined as described below. That is, with regard to a mixture obtained by adding 30 μL of a 0.1 wt % dispersion of the luminescent reagent to 60 μL of a buffer solution mixed with 16 μL of human serum diluted 15-fold, the absorbance of the mixture immediately after the addition is represented by A1, and the absorbance of the mixture after being left to stand at 37° C. for 5 minutes after the addition is represented by A2. The absorbances are measured at an optical path of 10 mm and a wavelength of 572 nm.

Particles showing an A2-A1 of 0.1 or less have little nonspecific adsorption of impurities in serum, and hence are preferred.

(Aqueous Medium)

The aqueous medium (aqueous solution) to be used for the above-mentioned method of producing the luminescent reagent preferably contains water at 80 wt % or more and 100 wt % or less in the medium. The aqueous solvent is preferably water or a water-soluble organic solvent, and examples thereof include solutions each obtained by mixing water with methanol, ethanol, isopropyl alcohol, or acetone. When an organic solvent other than water is incorporated at more than 20 wt %, there is a risk in that dissolution of the polymerizable monomers may occur at the time of the production of the particles.

In addition, the aqueous medium preferably has its pH adjusted to 6 or more and 9 or less in advance. When the pH has a value of less than 6 or more than 9, there is a risk in that an alkoxide group or silanol group of the radically polymerizable organic silane may undergo condensation polymerization or a reaction with another functional group before the formation of the polymer, leading to aggregation of the particles to be obtained. In this embodiment, the alkoxide is not intentionally subjected, before the polymerization, to condensation polymerization.

The above-mentioned pH is preferably adjusted using a pH buffer, but may be adjusted with an acid or a base.

Other than the foregoing, a surfactant, an antifoaming agent, a salt, a thickener, and the like may be used by being added at a ratio of 10% or less with respect to the aqueous medium.

In the production of the luminescent reagent, it is preferred that, first, the PVP be dissolved in the aqueous medium whose pH has been adjusted to from 6 to 9. The content of the PVP is preferably 0.01 wt % or more and 10 wt % or less, more preferably from 0.03 wt % to 5 wt % with respect to the aqueous medium. When the content is less than 0.01 wt %, the amount of adsorption onto the particle substrate is small, and the effect thereof is not expressed. In addition, when the content is more than 10 wt %, there is a risk in that the viscosity of the aqueous medium may be increased to preclude sufficient stirring.

Subsequently, the radically polymerizable monomers including the styrene (A) and the radically polymerizable organic silane (B) are added into the above-mentioned aqueous medium to prepare an emulsion. A weight ratio between the styrene (A) and the radically polymerizable organic silane (B) is from 6:4 to 100:1. Further, the prepared emulsion is mixed with the europium complex. At this time, when the solubility of the europium complex is low, a water-insoluble organic solvent may be added. A weight ratio between the europium complex and the radically polymerizable monomers is from 1:1,000 to 1:10.

When the weight ratio between the styrene (A) and the radically polymerizable organic silane (B) is less than 6:4, there is a risk in that the specific gravity of the particles as a whole may be increased, resulting in remarkable sedimentation of the particles. In addition, in order to increase adhesiveness between the PVP and luminescent particles, it is desired that the weight ratio between the styrene (A) and the radically polymerizable organic silane (B) be set to 100:1 or more.

A weight ratio between the weight of the aqueous medium and the total amount of the radically polymerizable monomers is preferably from 5:5 to 9.5:0.5. When the weight ratio between the weight of the aqueous medium and the total amount of the radically polymerizable monomers is less than 5:5, there is a risk in that remarkable aggregation of the particles to be produced may occur. In addition, when the weight ratio between the weight of the aqueous medium and the total amount of the radically polymerizable monomers is more than 9.5:0.5, although there is no problem with the production of the particles, there is a risk in that the production amount thereof may be reduced.

The radical polymerization initiator is used by being dissolved in water, a buffer, or the like. The radical polymerization initiator may be used between 0.5 mass % and 10 mass % in the emulsion with respect to the total weight of the styrene (A) and the radically polymerizable organic silane (B).

In the above-mentioned step of heating the emulsion, it is only required that the entire emulsion be uniformly heated. A heating temperature may be arbitrarily set between 50° C. and 80° C., and a heating time may be arbitrarily set between 2 hours and 24 hours. Through the heating of the emulsion, the radically polymerizable monomers are polymerized.

The luminescent reagent may have a ligand-bonding functional group on its surface. The ligand-bonding functional group is not particularly limited as long as the functional group can bond an antibody, an antigen, an enzyme, or the like, but for example, may be a carboxy group, an amino group, a thiol group, an epoxy group, a maleimide group, a succinimidyl group, a silicon alkoxide group, or the like, or contain any of those functional groups. For example, a silane coupling agent having the ligand-bonding functional group and the synthesized particles may be mixed to provide the functional group on the particle surface. Specifically, an aqueous solution of a silane coupling agent having a carboxy group may be prepared and mixed with a dispersion of the synthesized particles to provide the carboxy group on the particle surface. At this time, a dispersant such as Tween 20 may be added to the reaction solution. A reaction temperature may be arbitrarily set between 0° C. and 80° C., and a reaction time may be arbitrarily set between 1 hour and 24 hours. In order to suppress an abrupt condensation reaction of the silane coupling agent, it is suitable that the temperature be set to be equal to or lower than a room temperature of about 25° C., and the reaction time be set to from about 3 hours to about 14 hours. Depending on the ligand-bonding functional group, the reaction with the particle surface may be promoted by adding an acid or alkali catalyst.

The luminescent reagent can be utilized as particles for a specimen test by bonding a ligand such as any of various antibodies thereto. An optimal technique for bonding an antibody of interest or the like through utilization of a functional group present on the hydrophilic layer 2 only needs to be selected.

(Introduction of Ligand)

A hitherto known method may be applied to a chemical reaction for chemically bonding the ligand-bonding functional group and the ligand to the extent that the object of the present invention can be achieved. In addition, when the ligand is amide-bonded, a catalyst such as 1-[3-(dimethylaminopropyl)-3-ethylcarbodiimide] may be appropriately used.

The luminescent reagent to be used in this embodiment may be preferably applied to a latex immunoagglutination measurement method utilized widely in the fields of clinical tests, biochemical research, and the like.

(Analysis Apparatus)

According to one embodiment of the present invention, there is provided the following analysis apparatus: an analysis apparatus for measuring a value (R) for polarization anisotropy through use of a luminescent reagent that reacts with a target substance, to thereby measure at least any one of the presence or absence of the target substance and a concentration of the target substance, the analysis apparatus including: a reaction unit configured to mix a sample containing the target substance with the luminescent reagent, and to subject the mixture to a reaction to obtain a reaction liquid; a dilution unit configured to dilute the reaction liquid to obtain a diluted liquid; a measurement unit configured to measure the R of the diluted liquid; and a control unit, the luminescent reagent including luminescent particles.

The analysis apparatus according to this embodiment is schematically illustrated in FIG. 2.

The reaction unit is a unit configured to perform the reaction step. The dilution unit is a unit configured to perform the dilution step. The measurement unit is a unit configured to perform the measurement step. The control unit is configured to control the reaction unit, the dilution unit, and the measurement unit. The control unit has the functions of a computer. For example, the control unit may be configured integrally with a desktop personal computer (PC), a laptop PC, a tablet PC, a smartphone, or the like. The control unit includes a CPU, a RAM, a ROM, and an HDD in order to realize functions as a computer configured to perform computation and storage, and may include a communication interface (I/F), a display device, and an input device.

(Reagent)

The analysis method according to this embodiment may be used for a specimen test or in vitro diagnosis. A reagent for such use may include the luminescent reagent to be used in this embodiment and a dispersion medium for dispersing the luminescent reagent. The amount of the luminescent reagent contained in the reagent is preferably from 0.000001 mass % to 20 mass %, more preferably from 0.0001 mass % to 1 mass %. The reagent may include, in addition to the luminescent reagent, a third substance, such as an additive or a blocking agent, to the extent that the object of the present invention can be achieved. The reagent may include a combination of two or more kinds of third substances, such as an additive and a blocking agent. Examples of the dispersion medium to be used in this embodiment include various buffer solutions, such as a phosphate buffer solution, a glycine buffer solution, a Good's buffer solution, a Tris buffer solution, and an ammonia buffer solution, but the dispersion medium included the reagent in this embodiment is not limited thereto.

When the reagent is used for the detection of an antigen or an antibody in a specimen, an antibody or an antigen may be used as the ligand.

EXAMPLES

The present invention is specifically described below by way of Examples. However, the present invention is not limited to these Examples.

(1) Production of Luminescent Particles

Polyvinylpyrrolidone (PVP-K30: manufactured by Tokyo Chemical Industry Co., Ltd.) was dissolved in a 2-morpholinoethanesulfonic acid (MES) buffer solution (manufactured by Kishida Chemical Co., Ltd.) having a pH of 7 to prepare a solvent A. [Tris(2-thenoyltrifluoroacetone)(bis(triphenylphosphineoxide))europium(III)] (manufactured by Central Techno Corporation, hereinafter abbreviated as "Eu $(TTA)_3(TPPO)_2$") serving as a europium complex, a styrene monomer (manufactured by Kishida Chemical Co., Ltd.), 3-methacryloxypropyltrimethoxysilane (manufactured by Tokyo Chemical Industry Co., Ltd., hereinafter abbreviated as "MPS") were mixed to prepare a reaction liquid B. The reaction liquid B was added into a four-necked flask containing the solvent A, and the mixture was stirred with a mechanical stirrer set to 300 rpm. After 15 minutes of stirring under a nitrogen flow condition, the temperature of an oil bath that had been prepared was set to 70° C., and the nitrogen flow was performed for an additional 15 minutes. After the mixed liquid had been heated and stirred, an aqueous solution having dissolved therein potassium persulfate (hereinafter abbreviated as "KPS") (manufactured by Sigma-Aldrich) was added into the reaction solution, and emulsion polymerization was performed for 20 hours. After the polymerization reaction, the resultant suspension was subjected to ultrafiltration with about 4 L of ion-exchanged water through use of an ultrafiltration membrane having a molecular weight cutoff of 100K to wash the product, to thereby provide a dispersion of luminescent particles.

An aliquot of the dispersion of the luminescent particles obtained by the emulsion polymerization was taken and added to an aqueous solution having dissolved therein 1 mass % of Tween 20 (manufactured by Kishida Chemical Co., Ltd.). After 10 minutes of stirring, a silane coupling agent, X12-1135 (manufactured by Shin-Etsu Chemical Co., Ltd.), was added, and the mixture was stirred overnight. After the stirring, the dispersion was centrifuged, the supernatant was removed, and the precipitate was redispersed with pure water. The operations of centrifugation and redispersion were performed 3 or more times to wash the product. The precipitate after the washing was redispersed in pure water. Thus, ligand-bonding functional groups were introduced into particles 1 to 8. A mass ratio among the particles, pure water, and X12-1135 loaded was set to 1:300:2.

(Production of Anti-CRP Antibody-Modified Luminescent Reagent)

An aliquot of 0.25 mL of the particle dispersion at 1.2 wt % corresponding to synthesized luminescent particles was taken, and the solvent was replaced by 1.6 mL of a MES buffer solution having a pH of 6.0. To the particle MES buffer solution, 1-[3-(dimethylamino)propyl]-3-ethylcarbodiimide and N-hydroxysulfosuccinimide sodium were added at 0.5 wt %, and the mixture was subjected to a reaction at 25° C. for 1 hour. After the reaction, the dispersion was washed with a MES buffer solution having a pH of 5.0, an anti-CRP antibody was added at 100 µg/mL, and the anti-CRP antibody was bonded to the particles at 25° C. for 2 hours. After the bonding, the particles were washed with a Tris buffer solution having a pH of 8. After the reaction, the particles were washed with a phosphate buffer solution to provide an anti-CRP antibody-modified luminescent reagent having a concentration of 0.3 wt % (sometimes referred to as "affinity particles").

(Production of Anti-TSH Antibody-Modified Luminescent Reagent)

An aliquot of 0.25 mL of the particle dispersion at 1.2 wt % corresponding to synthesized luminescent particles was taken, and the solvent was replaced by 1.6 mL of a MES buffer solution having a pH of 6.0. To the particle MES buffer solution, 1-[3-(dimethylamino)propyl]-3-ethylcarbodiimide and N-hydroxysulfosuccinimide sodium were added at 0.5 wt %, and the mixture was subjected to a reaction at 25° C. for 1 hour. After the reaction, the dispersion was washed with a MES buffer solution having a pH of 5.0, an anti-TSH antibody was added at 100 µg/mL, and the anti-TSH antibody was bonded to the particles at 25° C. for 2 hours. After the bonding, the particles were washed with a Tris buffer solution having a pH of 8. After the reaction, the particles were washed with a phosphate buffer solution to provide an anti-TSH antibody-modified luminescent reagent having a concentration of 1.0 wt % (sometimes referred to as "affinity particles"). The anti-TSH antibodies used were monoclonal antibodies, and the luminescent particles were modified with two kinds of anti-TSH antibodies in order to cause at least two or more particles to react with a TSH antigen serving as a measurement object.

The bonding of the antibodies to the particles was recognized by measuring the amount of a reduction in antibody concentration in the buffer solution having added thereto the antibodies by BCA assay.

Preparation of Luminescent Reagent Liquid

The anti-CRP antibody-modified luminescent reagent was diluted with a phosphate (PBS) buffer solution having a pH of 7.4 so as to have a concentration of 0.1 mg/mL to prepare a luminescent reagent liquid. In addition, the resultant anti-TSH antibody-modified luminescent reagent was diluted with a phosphate (PBS) buffer solution having a pH of 7.4 so as to have a concentration of 1.0 mg/mL to prepare a luminescent reagent liquid.

Preparation of Additional Liquid for Dilution

A 4-(2-hydroxyethyl)-1-piperazineethanesulfonic acid (HEPES) buffer solution and a PBS buffer solution were mixed at a ratio of 1:1 in terms of volume ratio to prepare an additional liquid for dilution.

Example 1

75 µL of the anti-CRP antibody-modified luminescent reagent liquid and 15 µL of a CRP antigen liquid were mixed, and the mixture was left to stand still at 37° C. for 10 minutes.

1,335 µL of the additional liquid for dilution at 37° C. was added to the mixture, followed by measurement of an R. The investigation was performed at a concentration of the CRP antigen of 200 pM. The measurement was performed using an apparatus 1 to be described later.

Example 2

30 μL of the anti-CRP antibody-modified luminescent reagent liquid and 30 μL of a CRP antigen liquid were mixed, and the mixture was left to stand still at 37° C. for 10 minutes.

An aliquot of 8 μL of the liquid is taken, and the aliquot is mixed with 392 μL of the additional liquid for dilution at 37° C., followed by measurement of an R. The investigation was performed at a concentration of the CRP antigen in the range of from 0 pM to 10.24 pM. The measurement was performed using an apparatus 2 to be described later.

Example 3

70 μL of the anti-TSH antibody-modified luminescent reagent liquid and 15 μL of a TSH antigen liquid were mixed, and the mixture was left to stand still at 37° C. for 10 minutes.

1,335 μL of the additional liquid for dilution at 37° C. was added to the mixture, followed by measurement of an R. The investigation was performed at a concentration of the TSH antigen of 1,600 pM. The measurement was performed using the apparatus 1 to be described later.

Comparative Example 1

15 μL of a CRP antigen liquid was mixed into 1,335 μL of the additional liquid for dilution, and the mixture was warmed at 37° C. 75 μL of the anti-CRP antibody-modified luminescent reagent liquid was added to the mixture, followed by measurement of an R. The investigation was performed at a concentration of the CRP antigen of 200 pM. The measurement was performed using the apparatus 1 to be described later.

Comparative Example 2

4 μL of a CRP antigen liquid was mixed into 392 μL of the additional liquid for dilution, and the mixture was warmed at 37° C. 4 μL of the anti-CRP antibody-modified luminescent reagent liquid was added to the mixture, followed by measurement of an R. The investigation was performed at a concentration of the CRP antigen in the range of from 0 pM to 10.24 pM. The measurement was performed using the apparatus 2 to be described later.

Comparative Example 3

15 μL of a TSH antigen liquid was mixed into 1,335 μL of the additional liquid for dilution, and the mixture was warmed at 37° C. 70 μL of the anti-TSH antibody-modified luminescent reagent liquid was added to the mixture, followed by measurement of an R. The investigation was performed at a concentration of the TSH antigen of 1,600 pM. The measurement was performed using the apparatus 1 to be described later.

(Evaluation)

The shape of each obtained luminescent reagent was evaluated using an electron microscope (S5500 manufactured by Hitachi High-Technologies Corporation).

The average particle diameter of the luminescent reagent was evaluated using dynamic light scattering (Zetasizer Nano S manufactured by Malvern).

The concentration of a suspension having the luminescent reagent dispersed therein was evaluated using a gravimetric analyzer (Thermo plus TG8120 manufactured by Rigaku Corporation).

Measurement of R was performed using the apparatus 1 and the apparatus 2. The apparatus 1 is an apparatus having such a configuration as described below.

An LED light source of excitation light at 340 nm was prepared, and a polarizing filter (manufactured by Sigma-koki Co., Ltd., NSPFU-30C) and a shortpass filter (manufactured by Edmund Optics, 84-706) were inserted into an optical path to set an optical system capable of irradiating a 1 cm quartz square cell. A polarizing filter (manufactured by Thorlabs, Inc., PIVISC050) and a bandpass filter (manufactured by Thorlabs, Inc., FB610-10) were set in a direction of 90° with respect to incident light. In order to measure luminescence as $I_{VV}$ and $I_{VH}$ in two directions at the same time, two sets in which the construction of a polarizer was changed by a direction of 90° with respect to incident light were prepared. For the detection of polarized light, spectrometry was performed using QEPro manufactured by Ocean Optics, Inc. Temperature control was set for a sample holder so as to enable measurement at 37° C. Measurement of a polarization anisotropic property was performed with the LED light source being fixed at an output of 12 mW and a cumulative time being set to 3 seconds. A measurement interval was set to 15 seconds. Based on the resultant fluorescence spectrum of polarized luminescence, a luminescence intensity in the wavelength range of from 600 nm to 630 nm was substituted into the equation (1) to determine an R.

The apparatus 2 is an apparatus having such a configuration as described below.

An LED light source of excitation light at 340 nm was prepared, and a polarizing filter (manufactured by Sigma-koki Co., Ltd., NSPFU-30C) and a shortpass filter (manufactured by Edmund Optics, 84-706) were inserted into an optical path to set an optical system capable of irradiating a quartz cell having an optical path length of 5 mm. For polarized luminescence emitted from a sample, the polarized light was separated into two directions by setting an excitation light cut filter (manufactured by Edmund Optics, 33-910), a polarizing beamsplitter (manufactured by Edmund Optics, 47-127), and a polarizer (manufactured by Sigmakoki Co., Ltd., SPF-30C-32) in the stated order in the optical path in a straight line with the excitation light across the sample. The separated polarized luminescence (in each of the two directions) was detected using an avalanche photodiode (APD, manufactured by Hamamatsu Photonics K.K., C15522-3010SA). Temperature control was set for a sample holder so as to enable measurement at 37° C. Measurement of a polarization anisotropic property was performed with the LED light source being fixed at an output of 60 mW and a cumulative time being set to 8 milliseconds. A measurement interval was set to 30 seconds. The resultant signals of the polarized luminescence was measured with an oscilloscope, and were substituted into the equation (1) to determine an R.

Nonspecific agglutination suppression evaluation of the luminescent reagent was performed as described below.

60 μl of a human serum solution diluted 15-fold with a buffer solution was added to the luminescent reagent dispersion (3 mg/mL), and the mixture was kept at a temperature of 37° C. for 5 minutes. An absorbance at 527 nm was measured before and after the temperature keeping, and the amount of change in absorbance before and after the temperature keeping was measured 3 times. Table 2 shows the average value of the 3 times. Evaluation was performed as follows: when the amount of change in "absorbancex 10,000" value was less than 1,000, it was determined that nonspecific agglutination was suppressed, and when the amount was 1,000 or more, it was determined that nonspecific agglutination occurred.

(Performance Evaluation)

The synthesized luminescent reagent had a particle diameter of about 100 nm, and showed strong red luminescence with excitation light at 340 nm.

According to the results of the nonspecific agglutination suppression evaluation, the change in absorbance was equal to or less than the specific numerical value (the amount of change in "absorbance×10,000" value was 1,000 or less), and hence it was recognized that the particles were capable of suppressing nonspecific adsorption.

Figure 4:
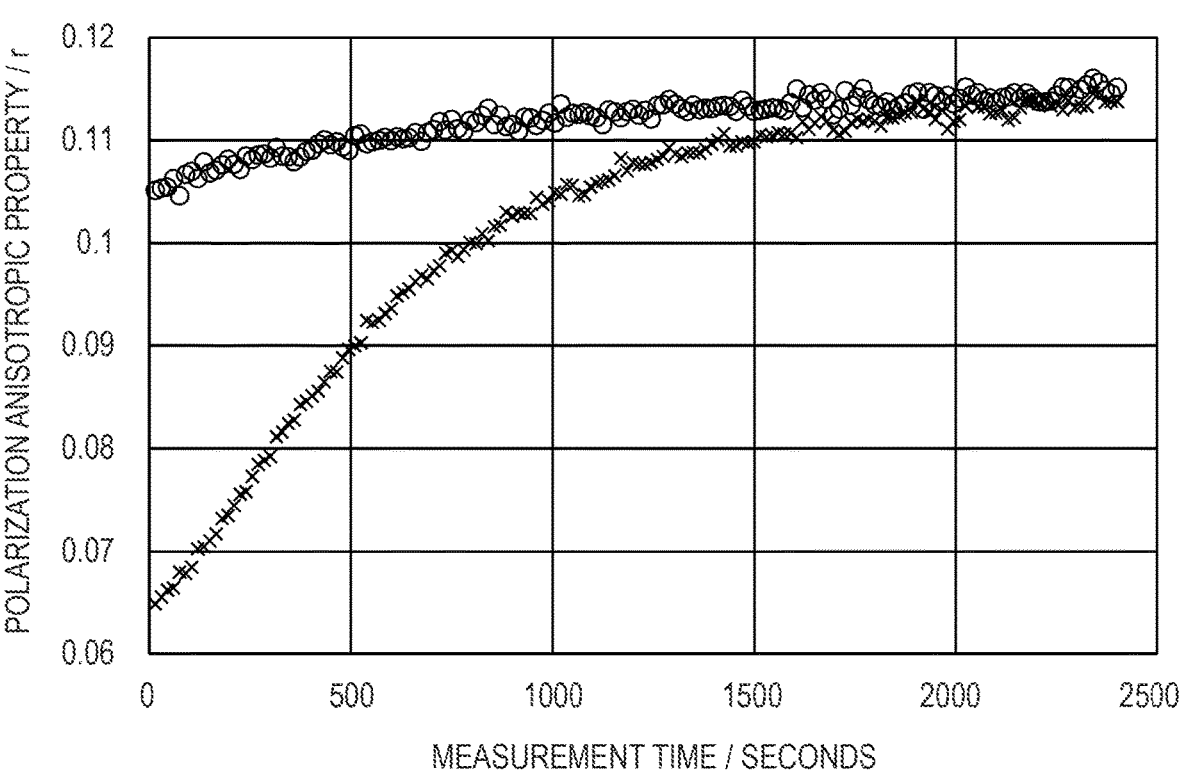
FIG. 4 is an explanatory graph of results of quantification of CRP antigen concentrations through use of the analysis method according to the embodiment of the present invention.

The results of Example 1 and Comparative Example 1 are shown in FIG. 4. FIG. 4 is a graph obtained by plotting the reaction time on the horizontal axis and the R (polarization anisotropic property "r") on the vertical axis. In Example 1, which is plotted with circles in FIG. 4, the "r" immediately after the measurement is more than 0.105, and then the "r" slowly increases. Meanwhile, in Comparative Example 1, which is plotted with "×" marks in FIG. 4, the "r" immediately after the measurement is 0.065, and an "r" comparable to that of Example 1 is found to be attained after a lapse of 2,000 seconds. Even when the reaction time in Example 1, i.e., 600 seconds is subtracted from 2,000 seconds, the antigen-antibody reaction of CRP proceeds faster in Example 1. Thus, it was able to be recognized that the R showed a high value within a short period of time.

Figure 5:
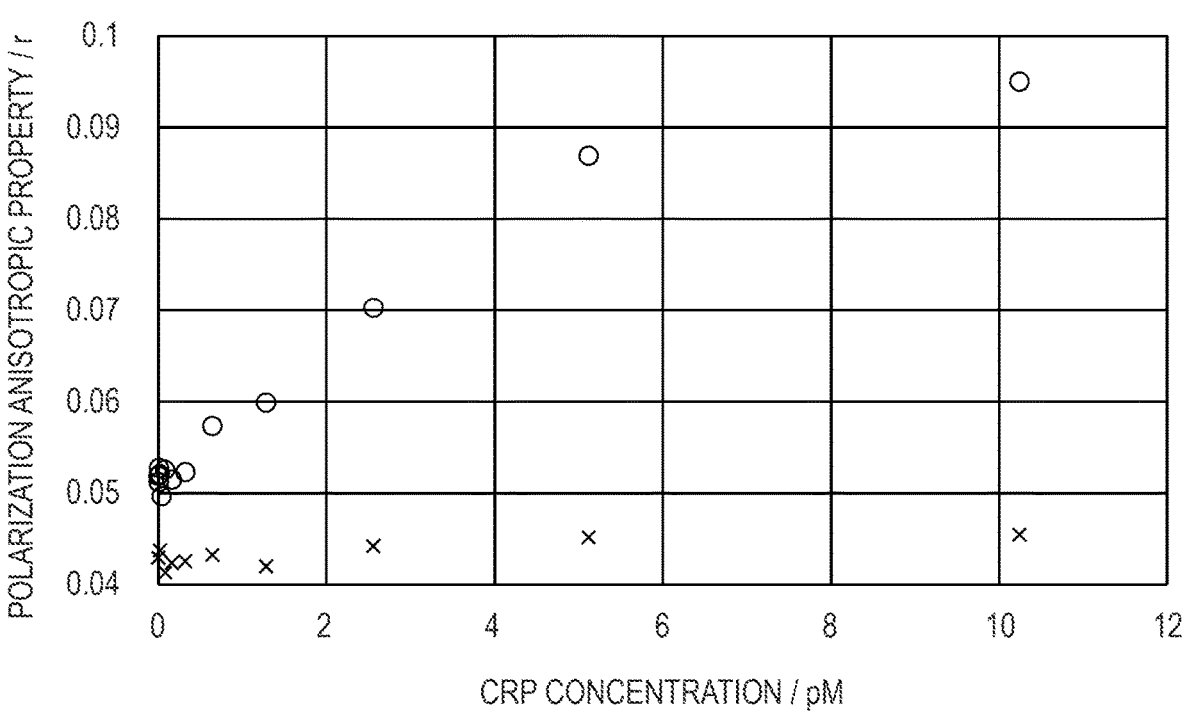
FIG. 5 is an explanatory graph of results of quantification of CRP antigen concentrations through use of the analysis method according to the embodiment of the present invention.

The results of Example 2 and Comparative Example 2 are shown in FIG. 5. FIG. 5 is a graph obtained by plotting the measured concentration of the CRP antigen on the horizontal axis and the polarization anisotropic property "r" 20 minutes later in reaction time on the vertical axis. The "reaction time" means a period of time measured with the time point of the mixing of the luminescent reagent and the CRP antigen being defined as zero.

It can be recognized that, in Example 2, which is plotted with circles in FIG. 5, the observed "r" also increases with an increase in CRP concentration. Meanwhile, in Comparative Example 2, which is plotted with "×" marks in FIG. 5, the "r" slightly increased, but had a slope with which the difference in "r" due to the CRP concentration was difficult to discern. In Example 2 and Comparative Example 2, the dilution factor was 10-fold higher than in Example 1 and Comparative Example 1, and the measured CRP concentrations were low. Accordingly, the difference in sensitivity due to the measurement method was also increased, and hence results showing a clearer difference were obtained.

The results of the investigations in Example 2 and Comparative Example 2 are shown in Table 1.

Table 1 shows that the change in polarization anisotropic property increased to 0.095 at a CRP antigen concentration of 10.24 pM in Example 2, but was only 0.045 in Comparative Example 2. In addition, a measurement lower limit value at which a calibration curve was able to be drawn from results and concentration measurement was possible was recognized down to 0.16 pM in Example 2, but was only down to about 10 pM in the measurement range in Comparative Example 2.

In Example 2 and Comparative Example 2, the kind and amount of the reagent used, and the measurement time were the same, but it was revealed that the presence or absence of an appropriate dilution step made a significant difference in measurement sensitivity.

TABLE 1

| Item | Example 2 | Comparative Example 2 |
|---|---|---|
| Measurement method | The luminescent reagent and the CRP antigen are mixed first and left to stand for 10 minutes, followed by the additional liquid for dilution. | The additional liquid for dilution and the CRP antigen are mixed first, immediately followed by mixing with the luminescent reagent. |
| Luminescent reagent concentration | 0.001 mg/mL | 0.001 mg/mL |
| CRP antigen concentration | 0 pM-10.24 pM | 0 pM-10.24 pM |
| Maximum value of change in "r" during 20 minutes | 0.095 | 0.045 |
| Measurable range | Down to about 0.16 pM | Down to about 10 pM |

Figure 6:
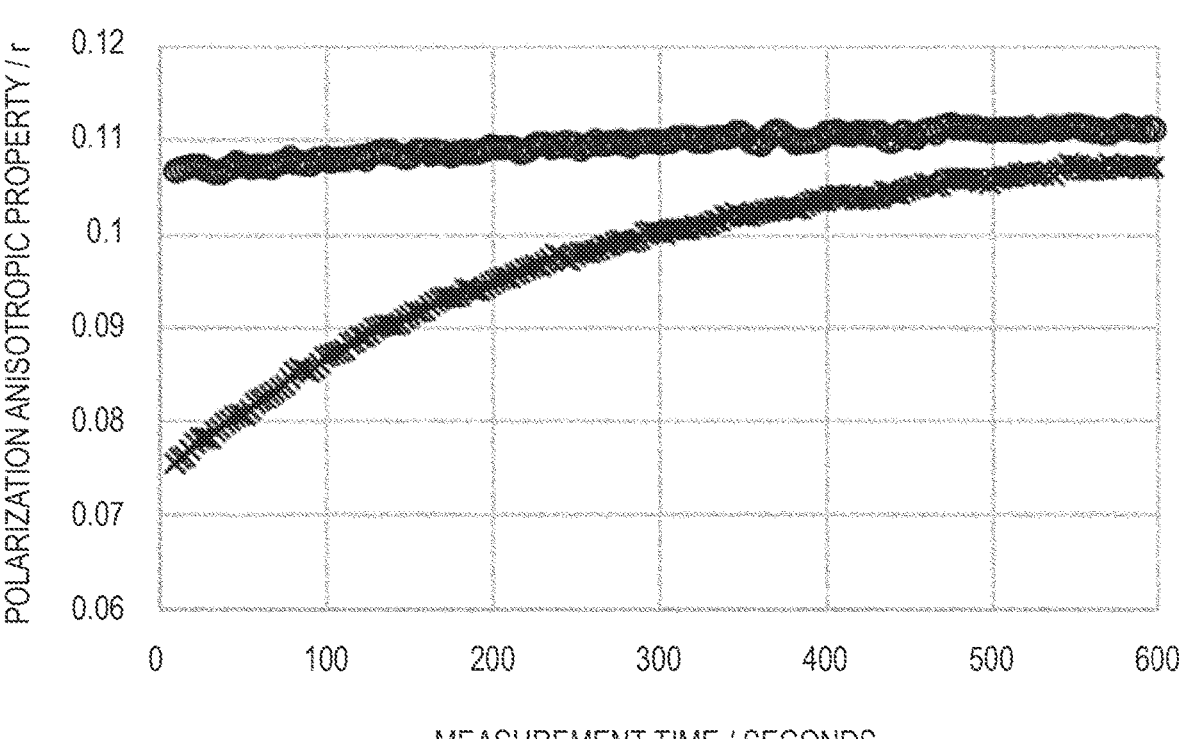
FIG. 6 is an explanatory graph of results of quantification of TSH antigen concentrations through use of the analysis method according to the embodiment of the present invention.

The results of Example 3 and Comparative Example 3 are shown in FIG. 6. FIG. 6 is a graph obtained by plotting the measurement time (i.e., the reaction time of the antibody included in the reagent, and the antigen) on the horizontal axis and the R (polarization anisotropic property "r") on the vertical axis. In FIG. 6, "○" represents the results of Example 3, and "×" represents the results of Comparative Example 3. In the plot of "○" in FIG. 6, the "r" immediately after the measurement is more than 0.106, and then the "r" slowly increases. Meanwhile, in the plot of "×" in FIG. 6, the "r" immediately after the measurement is 0.075, and an "r" comparable to that of Example 3 is found to be attained after a lapse of 600 seconds.

Thus, it was revealed that the measurement method according to Examples was a method capable of measuring the CRP antigen serving as a target substance with high sensitivity and within a short period of time.

Accordingly, the use of the measurement method according to Examples enables measurement of the target substance within a short period of time and with high sensitivity. It is conceived that the use of the measurement method according to Examples can realize an apparatus for performing measurement with high sensitivity in an application such as a specimen test in which mass testing is performed in a short period of time.

According to the analysis method according to the embodiment of the present invention, the sample containing the target substance and the luminescent reagent react in a concentrated state in the reaction step, and hence the reaction time can be shortened. Meanwhile, the reaction liquid is diluted through the dilution step, and hence scattering by the luminescent reagent is suppressed in the measurement step, to thereby enable high-sensitivity measurement. In addition, when the viscosity of the solution at the time of the measurement is excessively high, the value for polarization anisotropy is increased, and hence the change in R cannot be grasped as a large one, but this problem is also eliminated by providing the dilution step. In addition, it has further been found that the influence of multiple scattering can be further suppressed by shortening the optical path length of the optical system in the measurement of the R.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2022-079531, filed May 13, 2022, and Japanese Patent Application No. 2023-071430, filed Apr. 25, 2023, which are hereby incorporated by reference herein in their entirety.

What is claimed is:

1. An analysis method including measuring a value (R) for polarization anisotropy through use of a luminescent reagent that reacts with a target substance, to thereby determine at least any one of the presence or absence of the target substance and a concentration of the target substance, the analysis method comprising:

a reaction step including mixing a sample containing the target substance with the luminescent reagent, and subjecting the mixture to a reaction to obtain a reaction liquid;

a dilution step of diluting the reaction liquid to obtain a diluted liquid; and a measurement step of measuring the R of the diluted liquid, wherein the luminescent reagent includes in luminescent particles, and wherein the R is defined to be "r" in equation (1);

$$r = \frac{I_{VV} - G * I_{VH}}{I_{VV} + 2 * G * I_{VH}} \tag{1}$$

$$G = \frac{I_{HV}}{I_{HH}},$$

wherein:

$I_{VV}$ represents a luminescence intensity of a luminescence component having a vibration direction parallel to that of a first polarized light beam at a time of excitation by the first polarized light beam;

$I_{VH}$ represents a luminescence intensity of a luminescence component having a vibration direction orthogonal to that of the first polarized light beam at the time of excitation by the first polarized light beam;

$I_{HV}$ represents a luminescence intensity of a luminescence component having a vibration direction orthogonal to that of a second polarized light beam having a vibration direction orthogonal to that of the first polarized light beam at a time of excitation by the second polarized light beam;

$I_{HH}$ represents a luminescence intensity of a luminescence component having a vibration direction parallel to that of the second polarized light beam having a vibration direction orthogonal to that of the first polarized light beam at the time of excitation by the second polarized light beam; and G represents a correction value.

2. The analysis method according to claim 1, wherein the luminescent particles each contain a europium complex.

3. The analysis method according to claim 1, wherein the luminescent reagent contains a ligand that binds to the target substance.

4. The analysis method according to claim 3, wherein the ligand is an antibody, and the target substance is an antigen.

5. The analysis method according to claim 1, wherein R0≥0.001, where R0 represents the R measured for the luminescent reagent unreacted with the target substance.

6. The analysis method according to claim 1, wherein the dilution step comprises diluting the reaction liquid 2-fold or more.

7. The analysis method according to claim 1, wherein the diluting in the dilution step is performed so that the luminescent reagent is diluted to 0.05 mg/ml or less.

8. The analysis method according to claim 1, wherein the measuring the R is performed in an optical system having an optical path length of 5 mm or less.

9. An analysis apparatus for measuring a value (R) for polarization anisotropy through use of a luminescent reagent that reacts with a target substance, configured to measure at least any one of the presence or absence of the target substance and a concentration of the target substance, the analysis apparatus comprising:

a reaction unit configured to mix a sample containing the target substance with the luminescent reagent, and to subject the mixture to a reaction to obtain a reaction liquid;

a dilution unit configured to dilute the reaction liquid to obtain a diluted liquid; a measurement unit configured to measure the R of the diluted liquid; and a control unit, wherein the luminescent reagent includes including in luminescent particles, and wherein the R is defined to be "r" in equation (1);

$$r = \frac{I_{VV} - G * I_{VH}}{I_{VV} + 2 * G * I_{VH}} \tag{1}$$

$$G = \frac{I_{HV}}{I_{HH}},$$

wherein:

$I_{VV}$ represents a luminescence intensity of a luminescence component having a vibration direction parallel to that of a first polarized light beam at a time of excitation by the first polarized light beam;

$I_{VH}$ represents a luminescence intensity of a luminescence component having a vibration direction orthogonal to that of the first polarized light beam at the time of excitation by the first polarized light beam;

$I_{HV}$ represents a luminescence intensity of a luminescence component having a vibration direction orthogonal to that of a second polarized light beam having a vibration direction orthogonal to that of the first polarized light beam at a time of excitation by the second polarized light beam;

$I_{HH}$ represents a luminescence intensity of a luminescence component having a vibration direction parallel to that of the second polarized light beam having a vibration direction orthogonal to that of the first polarized light beam at the time of excitation by the second polarized light beam; and G represents a correction value.

* * * * *